United States Patent [19]

Böshagen et al.

[11] 4,156,729

[45] May 29, 1979

[54] 1,2-BENZISOTHIAZOLIN-3-ONES

[75] Inventors: Horst Böshagen, Haan; Ulrich Hörlein, Wuppertal, both of Fed. Rep. of Germany; Karl-August Meng, deceased, late of Wuppertal, Fed. Rep. of Germany, by Ilse H. F. Meng, legal representative; Friedel Seuter, Velbert, Fed. Rep. of Germany

[73] Assignee: Bayer Aktiengesellschaft, Fed. Rep. of Germany

[21] Appl. No.: 760,555

[22] Filed: Jan. 19, 1977

[30] Foreign Application Priority Data

Jan. 24, 1976 [DE] Fed. Rep. of Germany ....... 2602643

[51] Int. Cl.$^2$ ................... A61K 31/425; C07D 277/62
[52] U.S. Cl. ............................... 424/270; 260/304 A; 544/372; 546/209; 424/267; 424/250

[58] Field of Search ...................... 260/304 A, 293.57; 424/270

[56] References Cited

U.S. PATENT DOCUMENTS

| | | | |
|---|---|---|---|
| 3,227,715 | 1/1966 | Bub | 260/304 A |
| 4,113,728 | 9/1978 | Baggaley | 544/331 |

*Primary Examiner*—Donald G. Daus
*Assistant Examiner*—D. B. Springer
*Attorney, Agent, or Firm*—Jacobs & Jacobs

[57] ABSTRACT

6-Substituted-1,2-benzisothiazolin-3-ones carrying an aminoalkyl group in the 2-position and being optionally substituted in the 4- and/or 5-position are antithrombotic agents. The compounds, of which 2-(2-diethylaminoethyl)-4,5-dimethyl-1,2-benzisothiazolin-3-one is a representative embodiment, can be prepared by cyclization of an appropriately substituted bis-[2-(aminoalkylcarbamyl)phenyl]disulfide, or by other disclosed methods.

13 Claims, No Drawings

1,2-BENZISOTHIAZOLIN-3-ONES

The present invention pertains to new 1,2-benzisothiazolin-3-ones, to processes for their preparation and their use as anti-thrombotic agents and to compositions adapted to such medicinal use.

2-Aminoalkyl-1,2-benzisothiazolin-3-ones having antiphlogistic effects are disclosed in German Pat. No. 1,147,947. German Offenlegungsschrift No. 2,340,709 describes certain 1,2-benzisothiazolin-3-ones which exhibit antimicrobial effects. French Patent Specification 1,020-M and German Pat. No. 1,135,468 describe related benzisothiazolinones which exhibit growth-inhibiting or lethal effects on microorganisms.

The present invention pertains to 1,2-benzisothiazolin-3-ones of the formula:

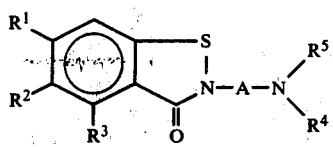

in which
- $R^1$ is halo, nitro, amino, alkyl, alkoxy, trifluoromethyl, alkylthio, a sulfonamide group which is optionally substituted by one or two alkyl groups, an optionally alkyl- or halo substituted aryl, aryloxy, arylthio or aralkoxy radical;
- $R^2$ is hydrogen, halo, alkyl, alkoxy or a sulfonamide group which is optionally substituted by alkyl; or
- $R^1$ and $R^2$ together are methylenedioxy or an aliphatic or aromatic ring;
- $R^3$ is hydrogen, halo, alkyl or alkoxy;
- A is an alkylene chain, which is straight-chain or branched, and which is optionally interrupted by an oxygen or sulfur atom; and
- each of $R^4$ and $R^5$ is alkyl or together are an alkylene chain, or one of $R^4$ or $R^5$ is joined to a carbon atom of the alkylene chain of A to form a pyrrolidine or piperidine ring, the rings formed by the substituents $R^4$ and $R^5$ being optionally substituted by alkyl or alkoxy, and optionally containing a second nitrogen atom, or a salt thereof.

Surprisingly, these new 1,2-benzisothiazolin-3-ones exhibit neither biocidal nor antiphlogistic properties as would have been expected from the similar 1,2-benzisothiazolin-3-ones known in the art. Instead, the present compounds exhibit powerful antithrombotic and thrombocyte aggregation inhibiting effects. Such effects have not previously been disclosed nor are they related to the effects previously described for benzisothiazolinones.

In a first embodiment therefore the present invention pertains to compounds of Formula I and the pharmaceutically acceptable acid addition salts thereof wherein
- $R^1$ when taken independently of $R^2$ is halo, nitro, amino, lower alkyl, lower alkoxy, trifluoromethyl, lower alkylthio, sulfonamido, lower alkylsulfonamido, di(lower alkyl)sulfonamido or an aromatic substituent selected from the group consisting of phenyl, phenoxy, benzyloxy and phenylthio which aromatic substituent is unsubstituted or substituted with halo or lower alkyl;
- $R^2$ when taken independently of $R^1$ is hydrogen, halo, lower alkyl, lower alkoxy, sulfamido, lower alkylsulfamido or di(lower alkyl)sulfamido;
- $R^1$ and $R^2$ taken together are alkylene of 3 to 5 carbon atoms or together with the two carbon atoms to which they are bound, benzo;
- $R^3$ is hydrogen, halo, lower alkyl or lower alkoxy;
- A when taken independently of $R^4$ is alkylene of 1 to 8 carbon atoms, alkylenoxyalkyl of 2 to 8 carbon atoms or alkylenethioalkyl of 2 to 8 carbon atoms;
- $R^4$ when taken independently of A and $R^5$ is lower alkyl; and
- $R^5$ when taken independently of $R^4$ is lower alkyl; or
- A and $R^4$ taken together are alkanetriyl of 3 to 8 carbon atoms or
- $R^4$ and $R^5$ taken together, together with the nitrogen atom to which they are bound are pyrrolidino, piperidono or N-(lower alkyl)piperazino.

In a second embodiment, the invention pertains to such compounds wherein
- $R^1$ when taken independently of $R^2$ is chloro, bromo, fluoro, nitro, amino, lower alkyl or an aromatic substituent selected from the group consisting of phenoxy, benzyloxy and phenylthio which aromatic substituent is unsubstituted or substituted with halo;
- $R^2$ when taken independently of $R^1$ is hydrogen, halo, lower alkyl or lower alkoxy;
- $R^1$ and $R^2$ taken together are trimethylene, tetramethylene or pentamethylene; and
- $R^3$ is hydrogen, halo, lower alkyl or lower alkoxy.

Within this second embodiment, a first preferred subclass are those compounds wherein
- A is alkylene of 2 to 5 carbon atoms, alkylenoxyalkyl of 4 to 8 carbon atoms or alkylenethioalkyl of 4 to 8 carbon atoms; and
- each of $R^4$ and $R^5$ is independently alkyl of 1 to 4 carbon atoms.

Within this second embodiment, a second preferred subclass are those compounds wherein
- A is alkylene of 2 to 5 carbon atoms, alkylenoxyalkyl of 4 to 8 carbon atoms or alkylenethioalkyl of 4 to 8 carbon atoms; and
- $R^4$ and $R^5$ together with the nitrogen atom to which they are bound are pyrrolidino, piperidino or N-methylpiperazino.

Within this second embodiment, a third preferred subclass are those compounds wherein
- A and $R^4$ taken together are alkanetriyl of 4 to 8 carbon atoms, there being at least 4 carbon atoms between the two bonds of said alkanetriyl bound to the nitrogen atom common to A and $R^4$; and
- $R^5$ is lower alkyl.

With this second embodiment, a fourth preferred subclass are those compounds wherein
- $R^1$ taken independently of $R^2$ is chloro, nitro, methyl, methoxy, ethoxy, butoxy, phenoxy, benzyloxy, phenylthio or chlorophenylthio;
- $R^2$ is hydrogen or methoxy; and
- $R^3$ is hydrogen or methyl.

It is to be appreciated by those actually working in medicinal chemistry that the foregoing classes and subclasses have been defined solely for ease of comprehension, structural correlation, and brevity of written expression in this specification. The invention naturally pertains to the actual physical embodiments, whether described individually, in any generic definition specifically depicted, or in any combination of one or more members of any of $R^1$, $R^2$, $R^3$, $R^4$, $R^5$ and A falling within the defined parameters of each such group for the common nucleus.

A further embodiment pertains to a method of achieving an antithrombotic effect in a human or other warm blooded animal which comprises administering thereto an antithrombotically effective amount of a compound according to the invention.

In another embodiment, the invention pertains to a pharmaceutical composition comprising an antithrombotically effective amount of a compound according to the invention in combination with a pharmaceutically acceptable carrier.

The term alkyl denotes a univalent saturated branched or straight hydrocarbon chain containing from 1 to 18 carbon atoms. Representative of such alkyl groups are thus methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

The term lower alkylthio denotes a branched or straight hydrocarbon chain of 1 to 6 carbon atoms bound to the remainder of the molecule through a divalent sulfur as, for example, methylthio, ethylthio, propylthio, isopropylthio, butylthio, and the like.

The term halo denotes the monovalent substituents fluoro, chloro, bromo and iodo.

As indicated, the present invention also pertains to the physiologically acceptable non-toxic acid addition salts of these basic compounds. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

When the side chain

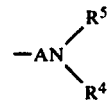

contains a center of chirality the compounds of the present invention can exist as optical isomers and both the racemates of these isomers and the individual isomers themselves are within the scope of the present invention. The racemates can be separated into their individual isomers through the well known technique such as forming diastereoisomeric salts.

The compounds can be prepared chemically in a number of ways.

In a first method, a disulfide of the formula:

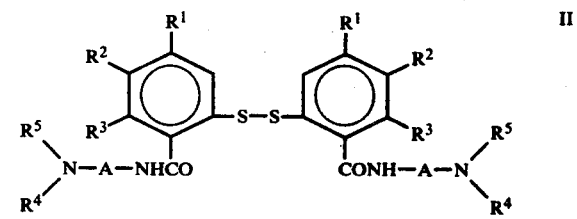

wherein $R^1$, $R^2$, $R^3$, $R^4$, $R^5$ and A are as defined above is subjected to oxidative cyclization utilizing chlorine, bromine or thionyl chloride as the cyclization agent or an aqueous alkaline solution as a disproportionation agent If 3,3'-5,5'-tetramethyldiphenyldisulfide-2,2'-dicarboxylic acid bis-N-(2-diethylaminoethyl)amide is used as the starting material and thionyl chloride as the oxidizing agent, the course of this reaction can be represented by the following equation:

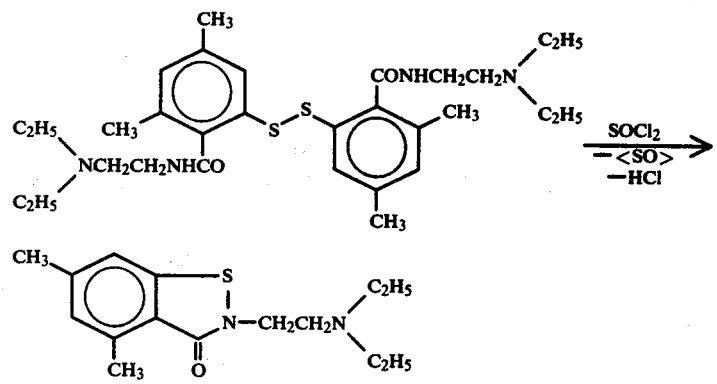

This process is carried out in an inert organic solvent at temperatures between 10° and 100° C., preferably between 20° and 80° C. The reaction time will be from 1 to 24 hours depending on the reaction temperature. The solvents are preferably halogenated hydrocarbons, especially carbon tetrachloride, choroform or methylene chloride. If thionyl chloride is used as the oxidizing agent, a 3-fold to 5-fold excess is preferably used. If chlorine or bromine is used as the oxidizing agent, an equivalent amount is preferably used. The reaction can be carried out under elevated pressure but generally normal pressure is used.

The diphenyldisulfide-2,2'-bis-carboxylic acid amides of Formula II are new. They can be readily prepared however in accordance with known methods, by first converting the corresponding 2-mercaptobenzoic acids into the diphenyldisulfide-2,2'-bis-carboxylic acid chloride by means of SOCl$_2$ and then reacting these chlorides with the appropriate basic amine in ethanol solution. See, e.g. U.S. Pat. No. 3,574,858.

In the compounds of Formula II,

- $R^1$ is preferably halo, especially fluoro, chloro or bromo, alkoxy of 1 to 6 carbon atoms, especially with 1 to 4 carbon atoms, benzoxy, nitro, amino, alkyl of 1 to 4 carbon atoms, phenoxy or thiophenyl, optionally substituted by halogen, especially fluoro or chloro;
- $R^2$ is preferably hydrogen, alkyl of 1 to 4 carbon atoms, especially methyl or ethyl, halo, especially fluoro or chloro, or methoxy or ethoxy; or
- $R^1$ and $R^2$ together are preferably an alkylene radical of 3 to 5 carbon atoms, especially tetramethylene;
- $R^3$ is preferably hydrogen, alkyl of 1 to 4 carbon atoms, especially methyl or ethyl, chloro, methoxy or ethoxy;
- A is preferably alkylene of 1 to 8 carbon atoms, especially of 1 to 5 carbon atoms, which is optionally interrupted by an oxygen atom or sulfur atom; and
- $R^4$ and $R^5$ are preferably alkyl of 1 to 4 carbon atoms, especially methyl or ethyl, or jointly alkylene of 4 or 5 carbon atoms, or one of $R^4$ or $R^5$ is bonded to a carbon atom of the alkylene chain (A) to form a pyrrolidine or piperidine ring, the rings thus formed being optionally substituted by methyl.

In addition to the diphenyl-2,2'-bis-carboxylic acid amides set forth in the examples, the following compounds can be employed in this process: 5,5'-dichlorodiphenyldisulfide-2,2'-dicarboxylic acid bis-N-(3-diethylaminopropyl)amide, 5,5'-dibromodiphenyldisulfide-2,2'-dicarboxylic acid bis-N-(3-diethylaminopropyl)amide, 5,5'-dichlorodiphenyldisulfide-2,2'-dicarboxylic acid bis-N-(3-dimethylaminopropyl)amide, 5,5'-dichlorodiphenyldisulfide-2,2'-dicarboxylic acid bis-N-(2-diethylaminoethyl)amide, 4,5,4',5'-tetrachlorodiphenyldisulfide-2,2'-dicarboxylic acid bis-N-(3-diethylaminopropyl)amide, 3,5,3',5'-tetrachlorodiphenyldisulfide-2,2'-dicarboxylic acid bis-N-(3-dimethylaminopropyl)amide, 3,5,3',5'-tetramethoxydiphenyldisulfide-2,2'-dicarboxylic acid bis-N-(2-diethylaminoethyl)amide, 4,5,4',5'-dimethylenedioxydiphenyldisulfide-2,2'-dicarboxylic acid bis-N-(3-diethylaminopropyl)amide, 4,5,4',5'-tetraethoxydiphenyldisulfide-2,2'-dicarboxylic acid bis-N-(3-diethylaminopropyl)amide, 5,5'-diphenylethoxydiphenyldisulfide-2,2'-dicarboxylic acid bis-N-(3-diethylaminopropyl)amide, 5,5'-bis-phenyldiphenyldisulfide-2,2'-dicarboxylic acid bis-N-(3-diethylaminopropyl)amide, 5,5'-dimethyldiphenyldisulfide-2,2'-dicarboxylic acid bis-N-(2-diethylaminoethyl)amide, 5,5'-diethyldiphenyldisulfide-2,2--dicarboxylic acid bis-N-(3-diethylaminopropyl)amide, 5,5'-dibutyldiphenyldisulfide-2,2'-dicarboxylic acid bis-N-(3-diethylaminopropyl)amide, 4,5,4',5'-tetramethyldiphenyldisulfide-2,2'-dicarboxylic acid bis-N-(3-diethylaminopropyl)amide and 4,5,4',5'-tetramethyldiphenyldisulfide-2,2'-dicarboxylic acid bis-N-[2-(2-diethylaminoethoxy)ethyl]amide.

According to a second process a phenylsulfenyl halide of the formula:

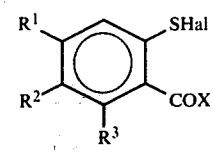

in which
- $R^1$, $R^2$ and $R^3$ are as above defined; Hal is chloro or bromo; and
- X is a leaving group, such as chloro, bromo, alkoxy or alkylthio, is allowed to react with an amine of the formula:

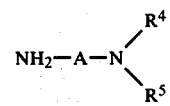

in which $R^4$, $R^5$ and A are as defined above, in the presence of inert organic solvents.

If 3-chloro-6-chlorocarbonylphenylsulfenyl chloride and 3-dimethylaminopropylamine are used as the starting material, the course of this reaction can be represented by the following equation:

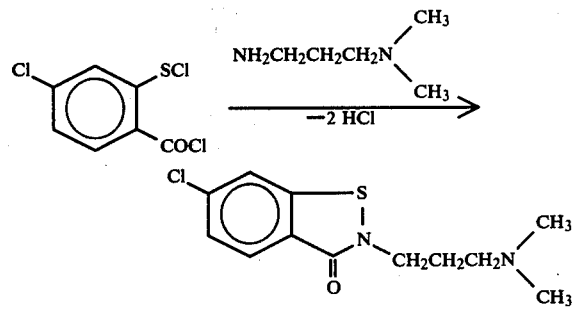

The process is suitably carried out by allowing 2-(6)-chlorocarbonylphenylsulfenyl chloride, dissolved in an inert organic solvent, to react with an equivalent amount of a basic amine, the amine dissolved in an inert organic solvent being introduced dropwise. Particularly suitable inert organic solvents are ethers such as tetrahydrofuran and diethyl ether, halogenated hydrocarbons such as chloroform, methylene chloride or carbon tetrachloride, alcohols such as methanol or ethanol, and hydrocarbons such as benzene, petrols or toluene. The reaction is preferably carried out in a temperature range of between 0° and 80° C., especially between 10° and 40° C. The reaction time can be varied within a substantial range, depending upon the reaction temperature, and is generally about 1 to 6 hours. The reactants are preferably employed in equivalent amounts. The reaction can be carried out under elevated pressure but in general, normal pressure is used.

The amines employed in this process are known.

The phenylsulfenyl halides of Formula III have been previously described but can be prepared from the corresponding diphenyldisulfide-2,2'-dicarboxylic acid chlorides by reaction with chlorine or bromine at room temperature in an inert solvent such as, for example, carbon tetrachloride; see, e.g. McClelland et al., J. Chem. Soc., 1926, 921.

In the compounds of Formula III,
Hal is chloro or bromo and

X is preferably chloro, bromo, alkoxy with 1 to 4 carbon atoms, especially methoxy or ethoxy, or alkylthio, especially methylthio.

The phenylsulfenyl halides include: 3-bromo-6-chlorocarbonylphenylsulfenyl chloride, 3,4-dichloro-6-chlorocarbonylphenylsulfenyl chloride, 3,5-dichloro-6-chlorocarbonylphenylsulfenyl chloride, 3-methyl-6-chlorocarbonylphenylsulfenyl chloride, 3-ethyl-6-chlorocarbonylphenylsulfenyl chloride, 3,5-dimethyl-6-chlorocarbonylphenylsulfenyl chloride, 3,4-dimethyl-6-chlorocarbonylphenylsulfenyl chloride, 3,4-tetramethylene-6-chlorocarbonylphenylsulfenyl chloride, 3-methoxy-4-chloro-6-chlorocarbonylphenylsulfenyl chloride, 3-methoxy-6-chlorocarbonylphenylsulfenyl chloride, 3-ethoxy-6-chlorocarbonylphenylsulfenyl chloride, 3-n-butoxy-6-chlorocarbonylphenylsulfenyl chloride, 3,4-diethoxy-6-chlorocarbonylphenylsulfenyl chloride, 3,4-dimethoxy-6-chlorocarbonylphenylsulfenyl chloride, 3,4-methylenedioxy-6-chlorocarbonylphenylsulfenyl chloride, 3-benzyloxy-6-chlorocarbonylphenylsulfenyl chloride, 3-($\beta$-phenethoxy)-6-chlorocarbonylphenylsulfenyl chloride and 3-nitro-6-chlorocarbonylphenylsulfenyl chloride.

In a third process, a 1,2-benzisothiazolin-3-one of the formula:

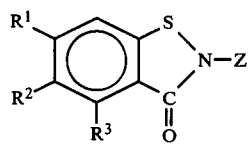

in which

R$^1$, R$^2$ and R$^3$ is as defined above;

Z is hydrogen or the —A—Y group, A having the above meaning, and

Y being a leaving radical, such as chloro, bromo, OSO$_2$-aryl or OSO$_2$-alkyl is allowed to react with an amine of the formula:

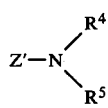

in which

R$^4$ and R$^5$ are as defined above; and

Z' is the same as Z, one of Z and Z' being hydrogen and the other being —A—Y, in an inert solvent at a temperature of from 20° to 120° C.

If 2-(3-chloropropyl)-6-chloro-1,2-benzisothiazolin-3-one and diethylamine are used as the starting material, the course of this reaction can be represented as follows:

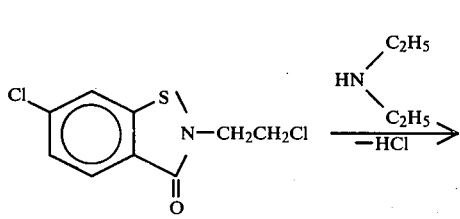

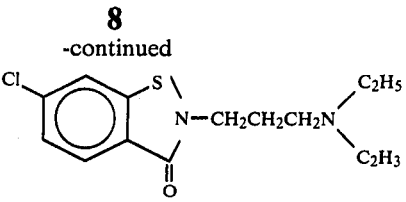

Preferably 1 mol of a 1,2-benzisothiazolin-3-one of Formula IV is allowed to react with about 1.5 mols of an amine of Formula V. The reaction is preferably carried out in the presence of inert organic solvents, especially in the presence of methyl ethyl ketone. Preferably, basic salts, especially alkali metal carbonates such as sodium or potassium carbonate, are added in a 2 to 4 mol excess as auxiliaries. The reaction temperature can be varied within a wide range. The reaction is carried out at temperatures between 20° and 120° C., especially between 50° and 100° C. The reaction time depends on the reaction temperature and will generally be 6 to 48 hours. Preferably, the reaction is carried out under normal pressure.

In the compounds of Formula V,

Y is preferably chloro, bromo, tosyl or alkylsulfonyloxy of 1 to 4 carbon atoms.

The amine compounds of Formula IV are known.

The 1,2-benzisothiazolin-3-ones of Formula IV are for the most part known but in any event can be prepared in accordance with known methods.

The following starting materials can be listed by way of example: 4,6-dichloro-1,2-benzisothiazolin-3-one; 2-(3-chloropropyl)-4,6-dichloro-1,2-benzisothiazolin-3-one; 4-chloro-6-methyl-1,2-benzisothiazolin-3-one; 2-(2-chloroethyl)-4-chloro-6-methyl-1,2-benzisothiazolin-3-one; 5,6-dichloro-1,2-benzisothiazolin-3-one and 2-(2-chloropropyl)-5,6-dichloro-1,2-benzisothiazolin-3-one.

Representative species of the present invention include: 2-(1-methylpyrrolid-3-ylmethyl)-6-chloro-1,2-benzisothiazolin-3-one; 2-(1-ethylpiperid-4-ylmethyl)-6-chloro-1,2-benzisothiazolin-3-one; 2-(1-methylpiperid-4-ylmethyl)-4,6-dimethyl-1,2-benzisothiazolin-3-one; 2-[1-(1-methylpiperid-4-yl)ethyl]-6-chloro-1,2-benzisothiazolin-3-one; 2-(1-methylpiperid-4-ylmethyl)-6-benzyloxy-1,2-benzisothiazolin-3-one; 2-(2-diethylaminoethyl)-6-benzyloxy-1,2-benzisothiazolin-3-one; 2-(3-diethylaminopropyl-6-benzyloxy-1,2-benzisothiazolin-3-one; 2-(1-methylpiperid-4-ylmethyl)-6-ethoxy-1,2-benzisothiazolin-3-one; 2-(2-diethylaminoethyl)-6-bromo-1,2-benzisothiazolin-3-one; 2-(1-methylpiperid-4-ylmethyl)-6-bromo-1,2-benzisothiazolin-3-one; 2-(2-diethylaminoethyl)-5,6-dichloro-1,2-benzisothiazolin-3-one; 2-(1-methylpiperid-4-ylmethyl)-5,6-dichloro-1,2-benzisothiazolin-3-one; 2-(2-diethylaminoethyl)-5,6-dibromo-1,2-benzisothiazolin-3-one; 2-(2-diethylaminoethyl)-6-trifluoro-methyl-1,2-benzisothiazolin-3-one; 2-(2-diethylaminoethyl)-5-bromo-6-methoxy-1,2-benzisothiazolin-3-one; 2-(1-methylpiperid-4-ylmethyl)-5-bromo-6-methoxy-1,2-benzisothiazolin-3-one; 2-(3-dimethylaminopropyl)-5-bromo-6-methoxy-1,2-benzisothiazolin-3-one; 2-(2-diethylaminoethyl)-5-bromo-6-isopropyl-1,2-benzisothiazolin-3-one; 2-(1-methylpiperid-4-ylmethyl)-6-trifluoromethyl-1,2-benzisothiazolin-3-one; 2-(2-diethylaminoethyl)-5,6-dimethyl-1,2-benzisothiazolin-3-one; 2-(2-diethylaminoethyl)-6-ethylthio-1,2-benzisothiazolin-3-one; 2-(2-diethylaminoethyl)-6-ethyl-1,2-benzisothiazolin-3-one; 2-(1-methylpiperid-4-ylmethyl)-6-ethyl-1,2-benzisothiazolin-3-one and 2-[2-(2-diethylaminoethoxy)ethyl]-6-ethoxy-1,2-benzisothiazolin-3-one.

The compounds of the invention, when administered orally or parenterally, produce a marked reduction in thrombocyte aggregation and in thrombotic deposits. They can accordingly be employed for the treatment and prophylaxis of thromboembolic conditions.

In general in the case of the parenteral route, administration of amounts of from about 0.01 to about 100 mg/kg of body weight per day, preferably about 0.1 to 10 mg/kg, produces a satisfactory response. In the case of oral administration a dosage of from about 0.5 to about 100 mg/kg of body weight per day, preferably 1.0 to 30 mg/kg, is adequate.

Nevertheless it may be necessary at times to deviate from the amounts mentioned, and in particular to do so as a function of body weight the route of administration, species, pharmaceutical response, the type of formulation and the time at or interval over which it is administered. In some cases, less than the above-mentioned minimum amount will suffice while in others, the upper limit mentioned may be exceeded. When it is desired to administer large amounts, it can be advisable to divide these into several individual administrations over the course of the day. As a general rule the amount administered should be such that the effective concentration in the plasma is of the magnitude of $10^{-3}$ mg/ml. Therefore the dose should be carefully titrated, utilizing sound professional judgment.

The biological action of the compounds can be conveniently observed and studied in recognized in vitro and in vivo models, of which the following are typical.

In vitro: Blood from healthy human test subjects of both sexes, and blood of rabbits and rats is used. One part of 3.8% strength aqueous sodium citrate solution, as an anticoagulant, is mixed with nine parts of blood. Centrifugation of this blood gives a platelet-rich citrate plasma (PRP); see generally Jürgens/Beller, Klinische Methoden der Blutgerinnungsanalyse, Thieme Verlag, Stuttgart (1959).

A mixture of 0.8 ml of PRP and 0.1 ml of the active compound solution is preincubated for 10 minutes at 37° C. Thrombocyte aggregation is then determined by the turbidimetric method of Born [J. Physiol. (London) 162, 67 (1962)] in an aggregometer at 37° C. [see generally Therapeutische Berichte, 47, 80–86 (1975)]. An aggregation-initiating agent (0.1 ml) such as collagen or ADP is thus added to the preincubated sample. The change in the optical density in the sample of PRP is recorded over a period of 6 minutes and the percentage inhibition is then calculated from the integrated area or the deflection.

Table I presents ranges of concentration at which the thrombocyte aggregation is inhibited by a value of 50% utilizing 2-(2-diethylaminoethyl)-4,6-dimethyl-1,2-benzisothiazolin-3-one (as the 1,5-naphthalenedisulfonate hemisalt) [compound A].

TABLE I
In Vitro Thrombocyte Aggregation Inhibition

| Aggregation-initiating agent | Active compound | $IC_{50}$ (g/ml) Human PRP | Rabbit PRP | Rat PRP |
|---|---|---|---|---|
| Collagen | Compound A | $1 \times 10^{-5}$–$3 \times 10^{-6}$ | $1 \times 10^{-6}$ | $3 \times 10^{-6}$–$1 \times 10^{-6}$ |
|  | Acetylsalicylic acid | $1 \times 10^{-5}$–$3 \times 10^{-6}$ | $1 \times 10^{-5}$–$3 \times 10^{-6}$ | $3 \times 10^{-6}$–$1 \times 10^{-6}$ |
|  | Dipyridamol | $1 \times 10^{-4}$–$3 \times 10^{-5}$ | — | — |
|  | Sulfinepyrazone | $1 \times 10^{-4}$–$3 \times 10^{-5}$ | — | — |
| ADP | Compound A | $3 \times 10^{-5}$–$1 \times 10^{-5}$ | $1 \times 10^{-6}$ | $1 \times 10^{-6}$ |
|  | Acetylsalicylic acid | $>1 \times 10^{-4}$ | $>1 \times 10^{-5}$ | $>1 \times 10^{-5}$ |
|  | Dipyridamol | $>1 \times 10^{-4}$ | — | $>1 \times 10^{-5}$ |
|  | Sulfinepyrazone | $>1 \times 10^{-4}$ | — | $>1 \times 10^{-5}$ |

The compounds also inhibit the adrenalin-induced, arachidonic acid-induced and thrombin-induced in vitro aggregation of the blood platelets.

Table II shows the percentage inhibition of the thrombocyte aggregation in PRP of rabbits and rats upon in vivo administration. In carrying out these experiments, the compound is administered orally in a tragacanth suspension. The animals are then bled, 90 minutes (rats) or 2 hours (rabbits), after administration, and the PRP is isolated by centrifuging. After isolating the PRP, the measurement of the aggregation inhibition is conducted in vitro analogously to the process described for Table I, without however any preincubation of the samples. Three parts of the rat PRP are furthermore diluted with 1 part of physiological sodium chloride solution.

TABLE II

| Test Compound | Species | Aggregation-initiator | Dose (oral) (mg/kg) | Percent inhibition (1) (integrated area) | (2) (amplitude) |
|---|---|---|---|---|---|
| Compound A | Rat | Collagen | 10 | 72* | 71* |
| Acetylsalicylic acid | Rat | Collagen | 10 | 31 | 35 |
| Dipyridamol | Rat | Collagen | 10 | 5 | 7 |
| Sulfinepyrazone | Rat | Collagen | 10 | −3 | 0 |
| Compound A | Rat | ADP | 30 | 45* | 77* |
| Acetylsalicylic acid | Rat | ADP | 30 | 15 | 27 |
| Dipyridamol | Rat | ADP | 30 | — | −23 |
| Sulfinepyrazone | Rat | ADP | 30 | — | −5 |
| Compound A | Rabbit | Collagen | 30 | 74* | 72* |
| Acetylsalicylic acid | Rabbit | Collagen | 30 | 63* | 58* |
| Compound A | Rabbit | ADP | 30 | 33* | 54* |
| Acetylsalicylic acid | Rabbit | ADP | 30 | 15 | 6 |

*=statistically significant (p 0.05)

Table III shows the percentage inhibition of thrombus formation in vivo. In this experiment, the left carotid artery of a rat is exposed and cooled to minus 15°

C. to stimulate thrombus formation. At the same time, the blood flow is reduced by means of a silver clip. The thrombus is isolated from the artery 4 hours later and is weighted. The table indicates the percentage reduction in weight of the thrombus when the test compound is administered immediately before the procedure.

TABLE III

| Test Compound | Dose (oral) (mg/kg) | Percentage inhibition |
|---|---|---|
| Compound A | 30 | 48 |
| Dipyridamol | 30 | 17 |

As is shown by Table I and II, the compounds according to the invention are powerful inhibitors of blood platelet aggregation. The compounds have a different action profile from that of acetylsalicylic acid, since not only collagen-induced aggregation but also the ADP-induced aggregation is inhibited. The clinically used inhibitors of ADP-induced aggregation, dipyridamol and sulfinepyrazone, are substantially less active in vitro and inactive at the tested doses in vivo.

As is shown by Table III, the compounds according to the invention also inhibit the formation of thrombus in animal experiments.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The following are examples of typical pharmaceutical formulations:

(a) Five hundred grams of 2-(2-diethylaminoethyl)-4,6-dimethyl-1,2-benzisothiazolin-3-one.½ 1,5-naphthalenedisulfonic acid are comminuted to a powder, mixed with 300 g of lactose and 200 g of potato starch, moistened with an aqueous gelatine solution and granulated through a sieve. After drying, 60 g of talc and 5 g of sodium laurylsulfate are added. The mixture is compressed to give 10,000 tablets having an active compound content of 50 mg each.

(b) Fifty grams of 2-(2-diethylaminoethyl)-4,6-dimethyl-1,2-benzisothiazolin-3-one.½ 1,5-naphthalenedisulfonic acid are dissolved in 1,000 ml of propylene glycol and the solution is made up to 2,000 ml with sterile water for injection. This solution is introduced under aseptic conditions, into sterile ampoules each of 5 ml volume, suitable to provide 50 mg of active compound for injection.

EXAMPLE 1

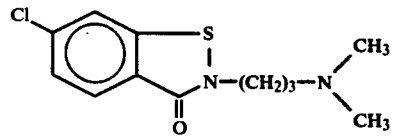

Twenty-two grams of the N,N'-bis(3-dimethylaminopropylamide) of 5,5'dichlorodiphenyldisulfide-2,2'-dicarboxylic acid as the dihydrochloride are dissolved in 50 ml of chloroform and 50 ml of thionyl chloride are slowly added dropwise. The mixture is allowed to stand for 18 hours at 35°–40° C. and then evaporated in vacuo. The residue is taken up in 100 ml of water and the insoluble constituents are removed by filtration. The aqueous solution is rendered alkaline by the addition of sodium hydroxide solution and the solid which precipitates is repeatedly extracted with ether. The ether extracts are dried and evaporated to yield, after recrystallization, 15.1 g of 2-(3-dimethylaminopropyl)-6-chloro-1,2-benzisothiazolin-3-one as colorless platelets, m.p. 69° C.; yield: 78%.

The corresponding hydrochloride is obtained upon addition of a solution of hydrochloric acid in ethanol, as colorless prisms which are recrystallized from ethanol, m.p. 208° C.

The starting compound can be prepared as follows:

(a) 5,5'-Dichlorodiphenyldisulfide-2,2'-dicarboxylic acid chloride 15.4 g of 4-chloro-2-mercaptobenzoic acid are introduced into 45 ml of thionyl chloride and the mixture is stirred for 5 hours at 60° C. until dissolution is complete. The excess thionyl chloride is then stripped off in vacuo. The crystalline residue, after recrystallization from benzene, has a melting point of 184° C.; yield: 12.6 g, 75% of theory.

(b) 5,5'-Dichlorodiphenyldisulfide-2,2'-dicarboxylic acid bis-N-(3-dimethylaminopropyl)amide.2HCl 20.6 g of 5,5'-dichlorodiphenyldisulfide-2,2'-dicarboxylic acid chloride are dissolved in 100 ml of tetrahydrofuran and the solution is added dropwise, at room temperature, to a solution of 5.1 g of 3-dimethylaminopropylamine in 100 ml of ethanol. The reaction solution is stirred for a further 2 hours and then concentrated by evaporation in vacuo. The resulting syrup slowly crystallizes out. The crude product can be cyclized without additional purification. After recrystallization from ethanol, the compound has a melting point of 204°, with decomposition.

Yield: 85% of theory.

The procedures of Examples 2–31 are conducted analogously to that of Example 1.

EXAMPLE 2

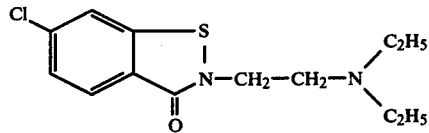

5,5'-Dichlorodiphenyldisulfide-2,2'-dicarboxylic acid bis-N-(2-diethylaminoethyl)amide gives 2-(2-diethylaminoethyl)-6-chloro-1,2-benzisothiazolin-3-one. Colorless prisms from cyclohexane; m.p. 78° C.; yield: 65% of theory.

Hydrochloride: colorless, knotty crystals from ethanol; m.p. 210° C.; yield: 90% of theory.

EXAMPLE 3

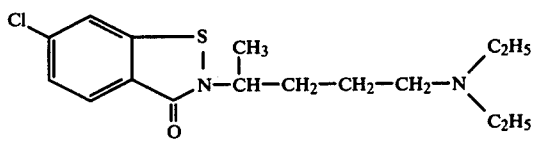

5,5'-Dichlorodiphenyldisulfide-2,2'-dicarboxylic acid bis-N-(4-diethylamino-1-methylbutyl)amide gives 2-(4-diethylamino-1-methylbutyl)-6-chloro-1,2-benzisothiazolin-3-one as a yellowish syrup.

$^1$H—NMR (60 MHz, in CDCl$_3$, TMS); CH$_3$ 8.95 (t, 6H): CH$_3$ 8.55 (d, 3H); N—CH$_2$—7.45 (q, 6H); —CH$_2$CH$_2$—8.35 (m, 4H); hetero—N—CH—5.10 (sextet, 1H);

aromatic protons 4—H 2.0 (d); 5—H 2.6 (d); 7—H 2.35 (s). Yield: 26% of theory.

EXAMPLE 4

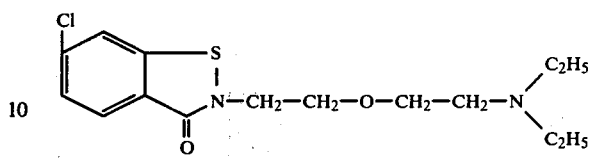

5,5'-Dichlorodiphenyldisulfide-2,2'-dicarboxylic acid bis-N-[2-(2-dimethylaminoethoxy)ethyl]amide gives 2-[2-(2-dimethylaminoethoxy)ethyl]-6-chloro-1,2-benzisothiazolin-3-one.½ 1,5-naphthalenedisulfonic acid: colorless crystals from water; m.p. 259°–260° C.; yield: 18% of theory.

EXAMPLE 5

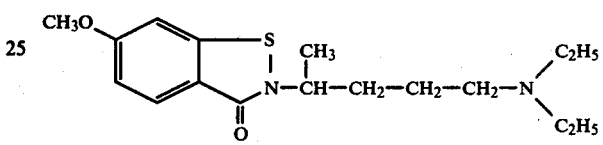

5,5'-Dimethoxydiphenyldisulfide-2,2'-dicarboxylic acid bis-N-(4-diethylamino-1-methylbutyl)amide gives 2-(4-diethylamino-1-methylbutyl)-6-methoxy-1,2-benzisothiazolin-3-one. ½ 1,5-naphthalenedisulfonic acid: colorless prisms from water; m.p. 218° C.; yield: 25% of theory.

EXAMPLE 6

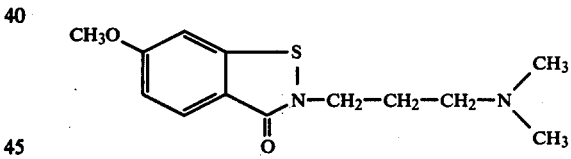

5,5'-Dimethoxydiphenyldisulfide-2,2'-dicarboxylic acid bis-N-(3-dimethylaminopropyl)amide gives 2-(3-dimethylaminopropyl)-6-methoxy-1,2-benzisothiazolin-3-one.½ 1,5-naphthalenedisulfonic acid: colorless prisms from ethanol (with addition of a trace of water); m.p. 288° C.; yield: 33.5% of theory.

EXAMPLE 7

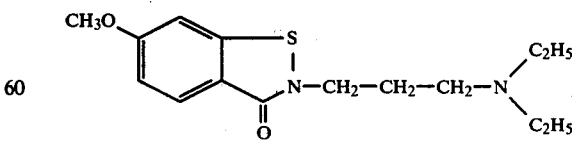

5,5'-Dimethoxydiphenyldisulfide-2,2'-dicarboxylic acid bis-N-(3-diethylaminopropyl)amide gives 2-(3-diethylaminopropyl)-6-methoxy-1,2-benzisothiazolin-3-one.½ 1,5-naphthalenedisulfonic acid, from methanol/acetone; colorless crystals; m.p. 288°–229° C.; yield: 15% of theory.

EXAMPLE 8

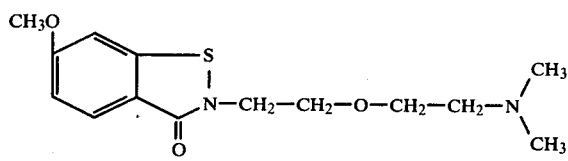

5,5′-Dimethoxydiphenyldisulfide-2,2′-dicarboxylic acid bis-N-[2-(2-dimethylaminoethoxy)ethyl]amide gives 2-[2-(2-dimethylaminoethoxy)ethyl]-6-methoxy-1,2-benzisothiazolin-3-one.oxalic acid: colorless crystals; m.p. 137°–138° C.; yield: 9% of theory.

EXAMPLE 9

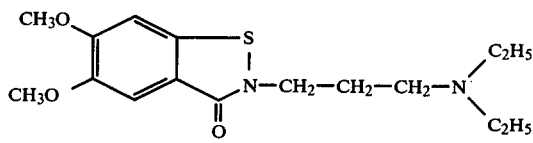

4,5,4′,5′-Tetramethoxydiphenyldisulfide-2,2′-dicarboxylic acid bis-N-(3-diethylaminopropyl)amide gives 2-(3-diethylaminopropyl)-5,6-dimethoxy-1,2-benzisothiazolin-3-one.oxalic acid: colorless crystals; m.p. 138°–140° C.; yield: 13% of theory.

EXAMPLE 10

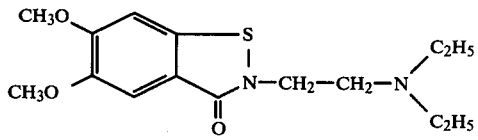

4,5,4′,5′-Tetramethoxydiphenyldisulfide-2,2′-dicarboxylic acid bis-N-(2-diethylaminoethyl)amide gives 2-(2-diethylaminoethyl)-5,6-dimethoxy-1,2-benzisothiazolin-3-one.½ 1,5-naphthalenedisulfonic acid: colorless crystals; m.p. 234°–235° C.; yield: 31% of theory.

EXAMPLE 11

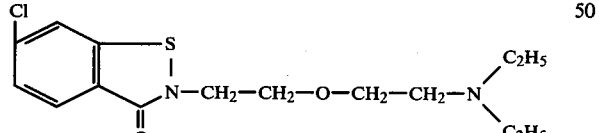

5,5′-Dichlorodiphenylsulfide-2,2′-dicarboxylic acid bis-N-[2-(2-diethylaminoethoxy)ethyl]amide gives 2-[2-(2-diethylaminoethoxy)ethyl]-6-chloro-1,2-benzisothiazolin-3-one as a yellowish oil; yield: 24% of theory.

EXAMPLE 12

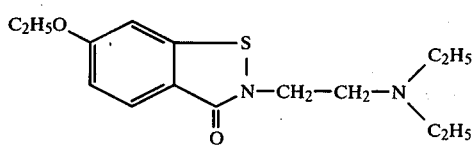

5,5′-Diethoxydiphenyldisulfide-2,2′-dicarboxylic acid bis-N-(2-diethylaminoethyl)amide gives 2-(2-diethylaminoethyl)-6-ethoxy-1,2-benzisothiazolin-3-one; colorless prisms from methanol; m.p. 88° C.; yield: 23% of theory.

EXAMPLE 13

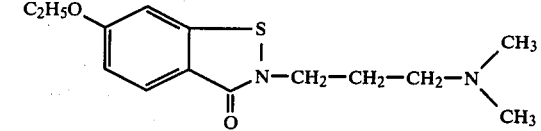

5,5′-Diethoxydiphenyldisulfide-2,2′-dicarboxylic acid bis-N-(3-dimethylaminopropyl)amide gives 2-(3-dimethylaminopropyl)-6-ethoxy-1,2-benzisothiazolin-3-one.½ 1,5-naphthalenedisulfonic acid: colorless prisms from ethanol with addition of a little water; m.p. 288° C.; yield: 35% of theory.

EXAMPLE 14

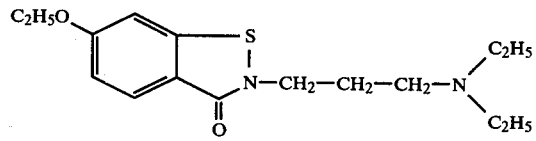

5,5′-Diethoxydiphenyldisulfide-2,2′-dicarboxylic acid bis-N-(3-diethylaminopropyl)amide gives 2-(3-diethylaminopropyl)-6-ethoxy-1,2-benzisothiazolin-3-one.½ 1,5-naphthalenedisulfonic acid: colorless prisms from water; m.p. 205° C.; yield: 26% of theory.

EXAMPLE 15

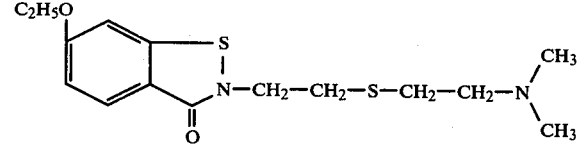

5,5′-Diethoxydiphenylsulfide-2,2′-dicarboxylic acid bis-N-[2-(2-dimethylaminoethylthio)ethyl]amide gives 2-[2-(2-dimethylaminoethylthio)ethyl]-6-ethoxy-1,2-benzisothiazolin-3-one as a yellowish oil.

EXAMPLE 16

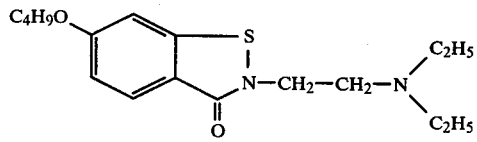

5,5′-Dibutoxydiphenyldisulfide-2,2′-dicarboxylic acid bis-N-(2-diethylaminoethyl)amide gives 2-(2-diethylaminoethyl)-6-n-butoxy-1,2-benzisothiazolin-3-one as a yellowish syrup. Molecular weight: 322 m/e ($C_{17}H_{26}N_2O_2S$) (determined by mass spectroscopy). Yield: 71.5% of theory.

EXAMPLE 17

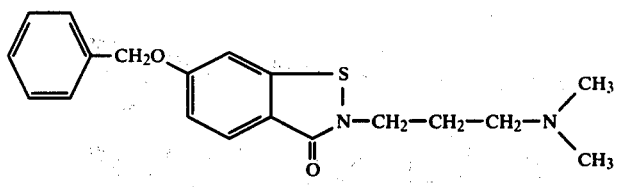

5,5′-Dibenzyloxydiphenyldisulfide-2,2′-dicarboxylic acid bis-N-(3-dimethylaminopropyl)amide gives 2-(3-dimethylaminopropyl)-6-benzyloxy-1,2-benzisothiazolin-3-one. Colorless flakes from ethyl acetate: m.p. 90° C.; yield: 15.5% of theory.

EXAMPLE 18

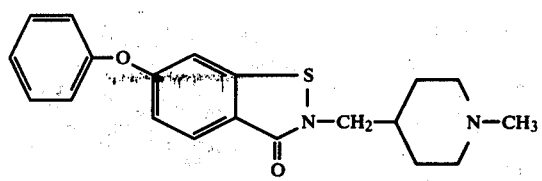

5,5′-Bis-phenoxydiphenyldisulfide-2,2′-dicarboxylic acid bis-N-(1-methylpiperid-4-ylmethyl)amide gives 2-(1-methylpiperid-4-ylmethyl)-6-phenoxy-1,2-benzisothiazolin-3-one.½ 1,5-naphthalenedisulfonic acid as crystals, m.p. 173° C.; yield: 11% of theory.

EXAMPLE 19

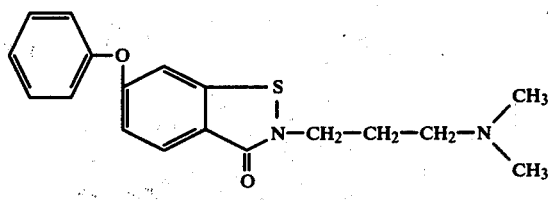

5,5′-Bis-phenoxydiphenyldisulfide-2,2′-dicarboxylic acid bis-N-(3-dimethylaminopropyl)amide gives 2-(3-dimethylaminopropyl)-6-phenoxy-1,2-benzisothiazolin-3-one as a yellowish oil; yield: 17% of theory.

EXAMPLE 20

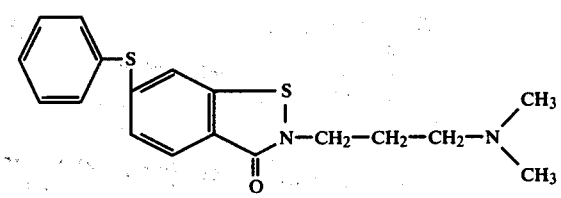

5,5′-Bis-phenylthiodiphenyldisulfide-2,2′-dicarboxylic acid bis-N-(3-diethylaminopropyl)amide gives 2-(3-diethylaminopropyl)-6-phenylthio-1,2-benzisothiazolin-3-one.oxalic acid: colorless crystals; m.p. 80° C.; yield: 26% of theory.

EXAMPLE 21

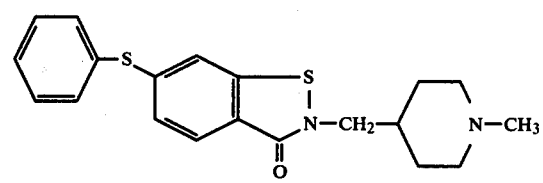

5,5′-Bis-phenylthiodiphenyldisulfide-2,2′-dicarboxylic acid bis-N-(1-methylpiperid-4-ylmethyl)amide gives 2-(1-methylpiperid-4-ylmethyl)-6-phenylthio-1,2-benzisothiazolin-3-one as a yellowish oil. Yield: 18% of theory.

EXAMPLE 22

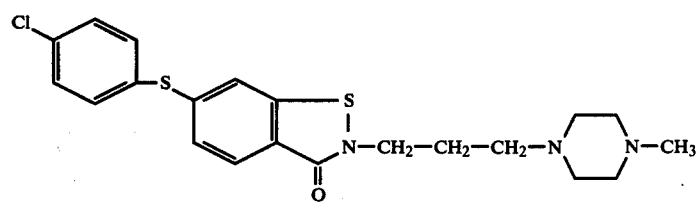

5,5′-Bis-(4-chlorophenylthio)diphenyldisulfide-2,2′-dicarboxylic acid bis-N-[3-(4-methylpiperazino)propyl]amide gives 2-[3-(4-methylpiperazino)propyl]-6-(4-chlorophenylthio)-1,2-benzisothiazolin-3-one.2-oxalic acid: colorless crystals; m.p. 206°–207° C.; yield: 35% of theory.

EXAMPLE 23

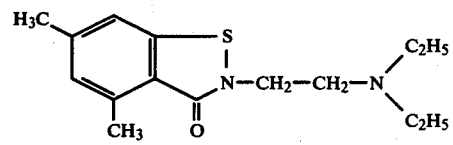

3,5,3′,5′-Tetramethyldiphenyldisulfide-2,2′-dicarboxylic acid bis-N-(2-diethylaminoethyl)amide gives 2-(2-diethylaminoethyl)-4,6-dimethyl-1,2-benzisothiazolin-3-one.hydrochloride: colorless, knotty crystals from methanol; m.p. 241° C.; yield: 36% of theory.

EXAMPLE 24

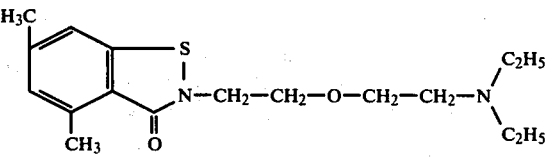

3,5,3′,5′-Tetramethyldiphenylsulfide-2,2-dicarboxylic acid bis-[2-(2-diethylaminoethoxy)ethyl]amide gives 2-[2-(2-diethylaminoethoxy)ethyl]-4,6-dimethyl-1,2-benzisothiazolin-3-one.oxalic acid: colorless crystals; m.p. 101°-102° C.; yield: 45% of theory.

EXAMPLE 25

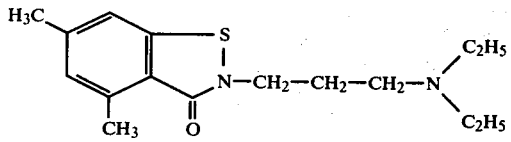

3,5,3′,5′-Tetramethyldiphenyldisulfide-2,2′-dicarboxylic acid bis-N-(3-diethylaminopropyl)amide gives 2-(3-diethylaminopropyl)-4,6-dimethyl-1,2-benzisothiazolin-3-one as a yellowish oil. $^1$H—NMR (60 MHz, in CDCl$_3$, TMS): CH$_3$, 9.05 (t, 6H); —CH$_2$—8.20 (q, 2H); N—CH$_2$ 7.50 (ml 6H); hetero-N—CH$_2$—6.20 (t, 2H); 4—CH$_3$-phenyl 7.30 (s, 3H); 6—CH$_3$-phenyl 7.70 (s, 3H); aromatic protons 5H 3.15 (s); 7H 2.90 (s). Yield: 23.5% of theory.

EXAMPLE 26

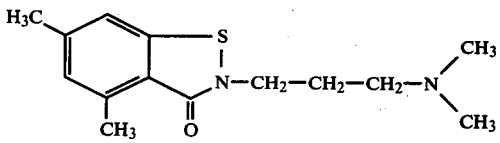

3,5,3′,5′-Tetramethyldiphenyldisulfide-2,2′-dicarboxylic acid bis-N-(3-dimethylaminopropyl)amide gives 2-(3-dimethylaminopropyl)-4,6-dimethyl-1,2-benzisothiazolin-3-one.½ 1,5-naphthalenedisulfonic acid: colorless, coarse prisms from ethanol; m.p. 204° C.; yield: 40% of theory.

EXAMPLE 27

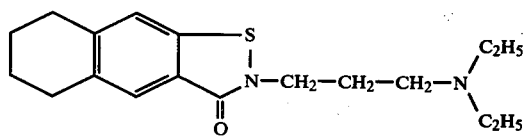

4,5,4′,5′-Bis-tetramethylenediphenyldisulfide-2,2′-dicarboxylic acid bis-N-(3-diethylaminopropyl)amide gives 2-(3-diethylaminopropyl)-5,6-tetramethylene-1,2-benzisothiazolin-3-one as a yellowish oil. Molecular weight=318 m/e (C$_{18}$H$_{26}$N$_2$OS) (determined by mass spectroscopy). Yield: 10% of theory.

EXAMPLE 28

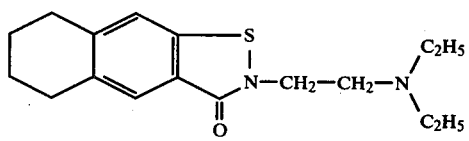

4,5,4′,5′-Bis-tetramethylenediphenyldisulfide-2,2′-dicarboxylic acid bis-N-(2-diethylaminoethyl)amide gives 2-(2-diethylaminoethyl)-5,6-tetramethylene-1,2-benzisothiazolin-3-one as a yellowish oil. Yield: 61% of theory. $^1$H—NMR (60 MHz, CDCl$_3$, TMS) CH$_3$ 8.95 (t, 6H); —CH$_2$—CH$_2$—8.20 (q, 4H); aromatic—CH$_2$ 7.20 (m, 4H);

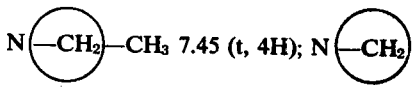

—CH$_2$—7.15 (t, 2H); hetero—N—CH$_2$—6.08 (t, 2H); aromatic protons 4—H 2.28 (s); 7—H 2.80 (s).

EXAMPLE 29

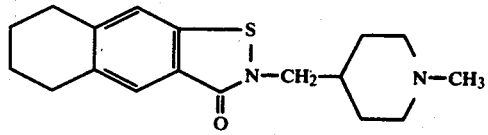

4,5,4′,5′-Bis-tetramethylenediphenyldisulfide-2,2′-carboxylic acid bis-N-(1-methylpiperid-4-ylmethyl)amide gives 2-(1-methylpiperid-4-ylmethyl)-5,6-tetramethylene-1,2-benzisothiazolin-3-one. Colorless crystals from petroleum ether; m.p. 109° C.; yield: 17% of theory.

EXAMPLE 30

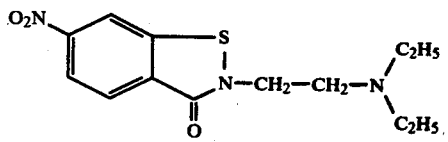

5,5′-Dinitrodiphenyldisulfide-2,2′-carboxylic acid bis-N-(2-diethylaminoethyl)amide gives 2-(2-diethylaminoethyl)-6-nitro-1,2-benzisothiazolin-3-one as light yellow, glossy flakes from ethanol; m.p. 132° C.; yield: 60.5% of theory.

EXAMPLE 31

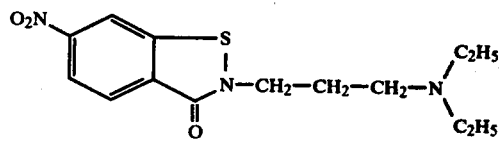

5,5′-Dinitrodiphenyldisulfide-2,2′-carboxylic acid bis-N-(3-diethylaminopropyl)amide gives 2-(3-diethylaminopropyl)-6-nitro-1,2-benzisothiazolin-3-one. Light yellow prisms from ligroin; m.p. 85° C.; yield: 15% of theory.

EXAMPLE 32

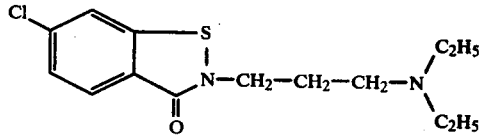

5,5′-Dichlorodiphenyldisulfide-2,2′-dicarboxylic acid bis-N-(3-diethylaminopropyl)amide is prepared analogously to Example 1b. To 31 g of the crude product in 100 ml of chloroform is added dropwise with stirring a solution of 8.0 g of bromine in 30 ml of carbon tetrachloride. The mixture is stirred for a further 2 hours and then evaporated in vacuo. The residue is boiled briefly with ethanol and the mixture is the re-evaporated. The residue is taken up in water, the insoluble matter is removed by filtration and the clear solution is rendered alkaline with sodium hydroxide solution. The solid which forms is taken up in ether and the ether solution is dried and evaporated; 13 g (48%).

The crude base is dissolved in 10 ml of methanol and precipitated as the naphthalenedisulfonate by adding 13 g of 1,5-naphthalenedisulfonic acid, dissolved in acetone. After recrystallization from ethanol, with addition of a trace of water, the disulfonate of 2-(3-diethylaminopropyl)-6-chloro-1,2-benzisothiazolin-3-one is obtained in the form of colorless flakes; m.p. 255° C.; yield: 85% of theory.

EXAMPLE 33

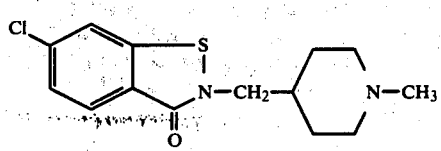

24.1 g of 3-chloro-6-chlorocarbonylphenylsulfenyl chloride are dissolved in 100 ml of tetrahydrofuran and the solution is added dropwise at 25° C., while stirring, to a solution of 5.8 g of N-methyl-4-aminomethylpiperidine and 10.0 g of triethylamine in 250 ml of ethanol. The mixture is stirred for 2 hours at room temperature and then evaporated in vacuo.

The residue is taken up in 250 ml of water and 20 ml of concentrated hydrochloric acid. Insoluble matter is separated off, the clear solution is rendered alkaline with sodium hydroxide solution and the solid which forms is taken up in ether. The ether extract is dried and evaporated. 12.6 g of 2-(1-methylpiperid-4-ylmethyl)-6-chloro-1,2-benzisothiazolin-3-one are obtained after recrystallization from ethanol; m.p. 144°-145° C.; yield: 42% of theory.

The required starting material, 3-chloro-6-chlorocarbonylphenylsulfenyl chloride, can be prepared as follows: (a) 100 g of 5,5'-dichlorodiphenyldisulfide-2,2'-dicarboxylic acid chloride are dissolved in 300 ml of carbon tetrachloride and 20 g of chlorine are passed in at 25° C. The batch is allowed to stand for 18 hours at room temperature. It is then filtered and the filtrate is evaporated in vacuo. The crude product is taken up in ligroin and the insoluble matter is discarded. After evaporation of the ligroin 85-95 g (72-81% of theory) of 3-chloro-6-chlorocarbonylphenylsulfenyl chloride are obtained as yellow needles; m.p. 86° C.

EXAMPLE 34

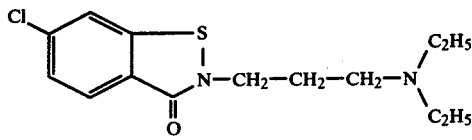

18.0 g of 2-(3-chloropropyl)-6-chloro-1,2-benzisothiazol-3-one are boiled for 15 hours in an excess of diethylamine in alcohol. The mixture is evaporated in vacuo and the residue is taken up in water, with addition of a little hydrochloric acid. Insoluble matter is filtered off and the clear solution is rendered alkaline with sodium hydroxide solution. The base which forms is taken up in ether and the ether solution is repeatedly washed with water, dried and evaporated.

2-(3-Diethylaminopropyl)-6-chloro-1,2-benzisothiazol-3-one is obtained as a yellowish syrup (65%). The hemi 1,5-naphthalenedisulfonic acid salt has a m.p. of 255° C.

2-(3-Chloropropyl)-6-chloro-1,2-benzisothiazol-3-one is obtained as follows:

(a) 26 g of 5,5'-dichlorodiphenyldisulfide-2,2'-dicarboxylic acid bis-N-(3-hydroxypropyl)amide of melting point 171° C. [prepared analogously to Ber. dtsch. chem. Ges. 99, 2,566 (1966)] are dissolved in 200 ml of thionyl chloride and the solution is stirred for half an hour at 30° C. and then for several hours at room temperature. The thionyl chloride is removed by distillation in vacuo and the residue is recrystallized from cyclohexane to yield 18.4 g of 2-(3-chloropropyl)-6-chloro-1,2-benzisothiazol-3-one (70% of theory); m.p. 89° C.

EXAMPLE 35

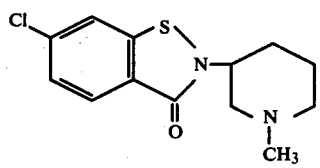

2-(1-Methylpiperid-3-yl)-6-chloro-1,2-benzisothiazolin-3-one is obtained analogously to Example 33 by reacting 3-chloro-6-chlorocarbonylphenylsulfenyl chloride with N-methyl-3-aminopiperidine [prepared analogously to Werbel et at. J. Het. Chem. 10, 381 (1973)]. The hydrochloride is recrystallized from methanol/acetone; m.p. 296°-297° C.; yield: 35% of theory.

EXAMPLE 36

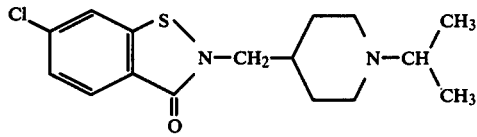

2-(1-sopropylpiperid-4-ylmethyl)-6-chloro-1,2-benzisothiazolin-3-one is obtained analogously to Example 33 by reacting 3-chloro-6-chlorocarbonylphenylsulfenyl chloride and 1-isopropyl-4-aminomethylpiperidine [boiling point $_{15}$:95°-97° C.; obtained from 4-acetylaminomethylpiperidine and isopropyl chloride analogously to Singh et al., J. Med. Chem. 12, 949 (1969) and Werbel et al., supra]. After recrystallization in acetone, yellow crystals of melting point 134°-135° C. are obtained; yield: 37% of theory.

What is claimed is:

1. A compound selected from the group consisting of 6-substituted 7-unsubstituted 1,2-benzisothiazolin-3-ones depicted by the formula:

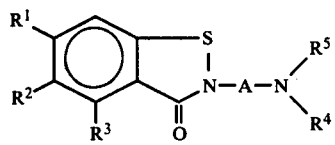

and the pharmaceutically acceptable acid addition salts thereof wherein $R^1$ when taken independently of $R^2$ is chloro, bromo, fluoro, nitro, alkyl of 1 to 4 carbon atoms, alkoxy of 1 to 4 carbon atoms or an aromatic substituent selected from the group consisting of phenoxy, benzyloxy and phenylthio which aromatic substituent is unsubstituted or nonsubstituted with alkyl of 1 to 4 carbon atoms or halo;

$R^2$ when taken independently of $R^1$ is hydrogen, alkyl of 1 to 4 carbon atoms or alkoxy of 1 to 4 carbon atoms;

$R^1$ and $R^2$ taken together are trimethylene, tetramethylene or pentamethylene;

$R^3$ is hydrogen, halo, alkyl of 1 to 4 carbon atoms or alkoxy of 1 to 4 carbon atoms;

each of $R^4$ and $R^5$ is alkyl of 1 to 4 carbon atoms; and

A is alkylene of 2 to 5 carbon atoms, alkylenoxyalkyl of 4 to 8 carbon atoms or alkylenethioalkyl of 4 to 8 carbon atoms.

2. A compound according to claim 1 wherein
$R^1$ taken independently of $R^2$ is chloro, nitro, methyl, methoxy, ethoxy, butoxy, phenoxy, benzyloxy, phenylthio or chlorophenylthio;
$R^2$ is hydrogen or methoxy; and
$R^3$ is hydrogen or methyl.

3. A compound according to claim 2 wherein
A is ethylene, trimethylene, tetramethylene, 1-methyltetramethylene, ethylenoxyethyl or ethylenethioethyl; and each of $R^4$ and $R^5$ is methyl or ethyl.

4. A compound according to claim 1 wherein
$R^1$ is chloro or methyl;
$R^2$ is hydrogen;
$R^3$ is hydrogen or methyl;
A is ethylene or trimethylene and each of $R^4$ and $R^5$ is methyl or ethyl.

5. A compound according to claim 1 wherein said 1,2-benzisothiazolin-3-one is 2-(3-dimethylaminopropyl)-6-chloro-1,2-benzisothiazolin-3-one.

6. A compound according to claim 1 wherein said 1,2-benzisothiazolin-3-one is 2-(2-diethylaminoethyl)-6-chloro-1,2-benzisothiazolin-3-one.

7. A compound according to claim 1 wherein said 1,2-benzisothiazolin-3-one is 2-(2-diethylaminoethyl)-4,6-dimethyl-1,2-benzisothiazolin-3-one.

8. A compound according to claim 1 wherein said 1,2-benzisothiazolin-3-one is 2-(3-diethylaminopropyl)-4,6-dimethyl-1,2-benzisothiazolin-3-one.

9. A compound according to claim 1 wherein said 1,2-benzisothiazolin-3-one is 2-(3-dimethylaminopropyl)-4,6-dimethyl-1,2-benzisothiazolin-3-one.

10. A compound according to claim 1 which is a salt of said 1,2-benzoisothiazolin-3-one with an acid selected from the group consisting of oxalic acid, 1,5-naphthalenedisulfonic acid, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicyclic acid, phthalic acid, embonic acid, and enanthic acid.

11. The method of achieving an antithrombotic effect in a human or other warm blooded animal in need thereof which consists essentially of administering thereto an antithrombotically effective amount of a compound according to claim 1.

12. A pharmaceutical composition consisting essentially of an antithrombotically effective amount of a compound according to claim 1 in combination with a pharmaceutically acceptable carrier.

13. A compound according to claim 1 wherein
$R^1$ is halo, alkyl of 1 to 4 carbon atoms or alkoxy of 1 to 4 carbon atoms;
$R^2$ is hydrogen; and
$R^3$ is hydrogen, halo or alkyl of 1 to 4 carbon atoms.

* * * * *

UNITED STATES PATENT AND TRADEMARK OFFICE
CERTIFICATE OF CORRECTION

PATENT NO. : 4,156,729
DATED : May 29, 1979
INVENTOR(S) : Horst Boshagen et al.

It is certified that error appears in the above—identified patent and that said Letters Patent are hereby corrected as shown below:

In claim 1, 7th line following formula, after "which", should read:

--aromatic substituent is unsubstituted or mono-substituted--

Signed and Sealed this

Eleventh Day of September 1979

[SEAL]

Attest:

LUTRELLE F. PARKER
Attesting Officer  Acting Commissioner of Patents and Trademarks